United States Patent [19]

Hadtke

[11] 4,004,734

[45] Jan. 25, 1977

[54] DISPENSER FOR AIR TREATING MATERIAL

[75] Inventor: Frederick B. Hadtke, New Providence, N.J.

[73] Assignee: Airwick Industries, Inc., Carlstadt, N.J.

[22] Filed: Oct. 3, 1975

[21] Appl. No.: 619,274

[52] U.S. Cl. .............................. 239/58; 220/23.4; 220/306; 230/315; 292/17
[51] Int. Cl.² ..................... A61L 9/00; B65D 21/02
[58] Field of Search .................. 239/34, 54–59, 239/60; 220/306, 315, 323, 23.4; 292/17, 19, 76, 80, 87

[56] References Cited

UNITED STATES PATENTS

| | | | |
|---|---|---|---|
| 947,584 | 1/1910 | Armstrong | 292/19 X |
| 2,311,040 | 2/1943 | Evert et al. | 292/17 |
| 2,765,951 | 10/1956 | Wheeler | 239/58 X |
| 3,651,976 | 3/1972 | Chadbourne | 220/23.4 |
| 3,908,906 | 9/1975 | Crowle et al. | 239/58 |

Primary Examiner—Evon C. Blunk
Assistant Examiner—Andres Kashnikow
Attorney, Agent, or Firm—Harry Falber

[57] ABSTRACT

A dispenser for solid air treating materials having a base container for the material and a displaceable cover. The base contains a socket which is adapted to receive prongs which project from the underside of the cover and to engage the prongs so as to permit the positioning of the cover in different vertically spaced positions with respect to the container and thereby to effect a corresponding release of air treating material.

11 Claims, 8 Drawing Figures

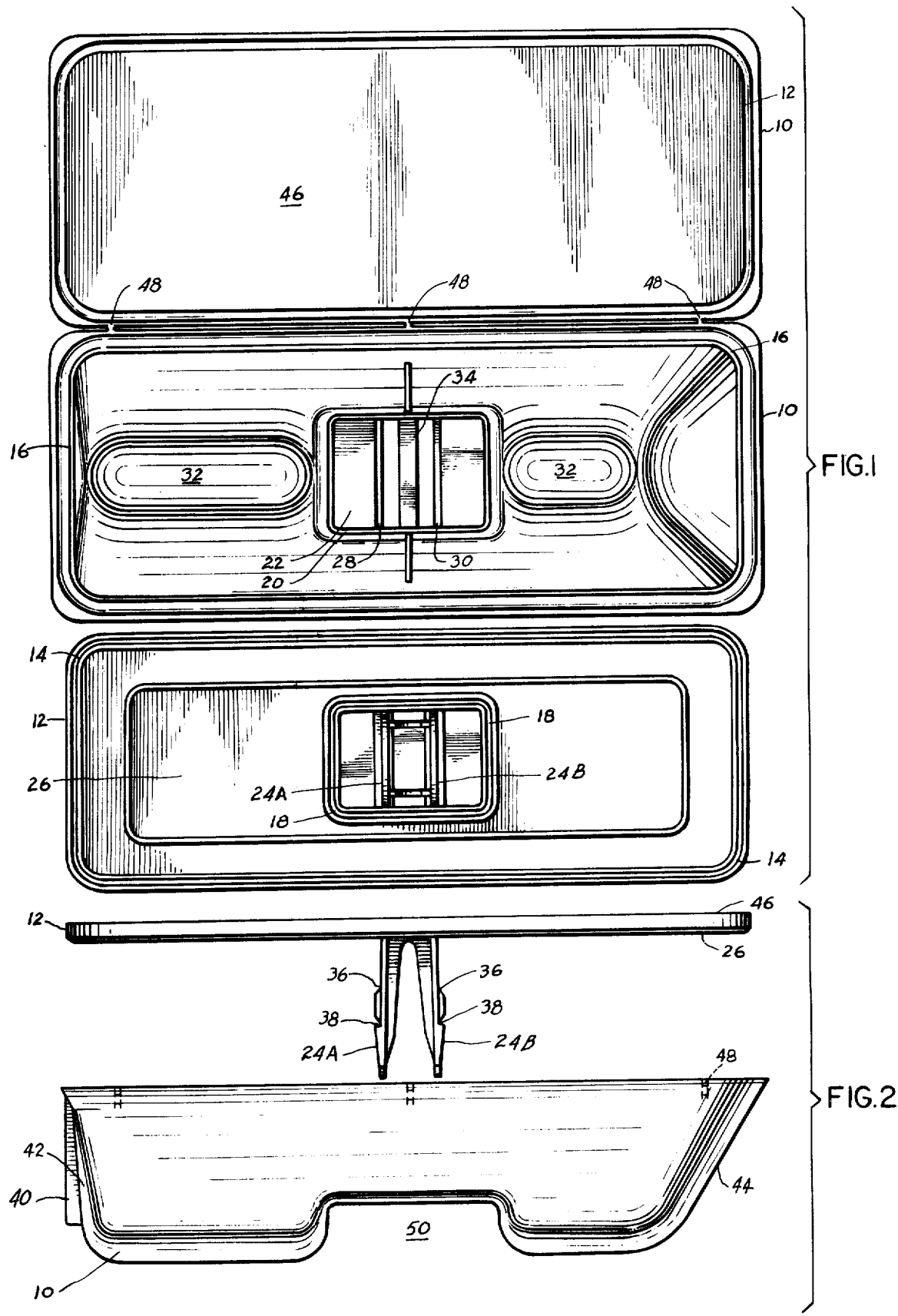

U.S. Patent   Jan. 25, 1977   Sheet 2 of 3   4,004,734
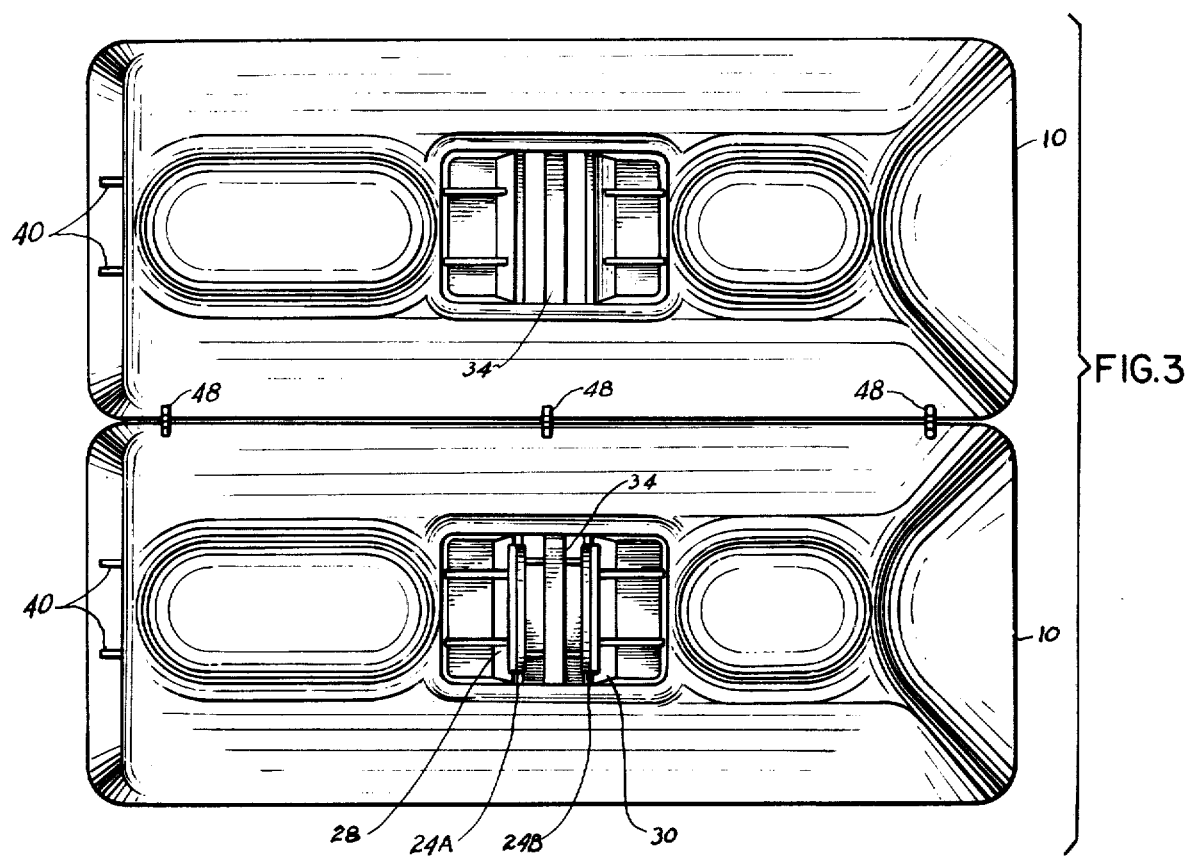
FIG. 3
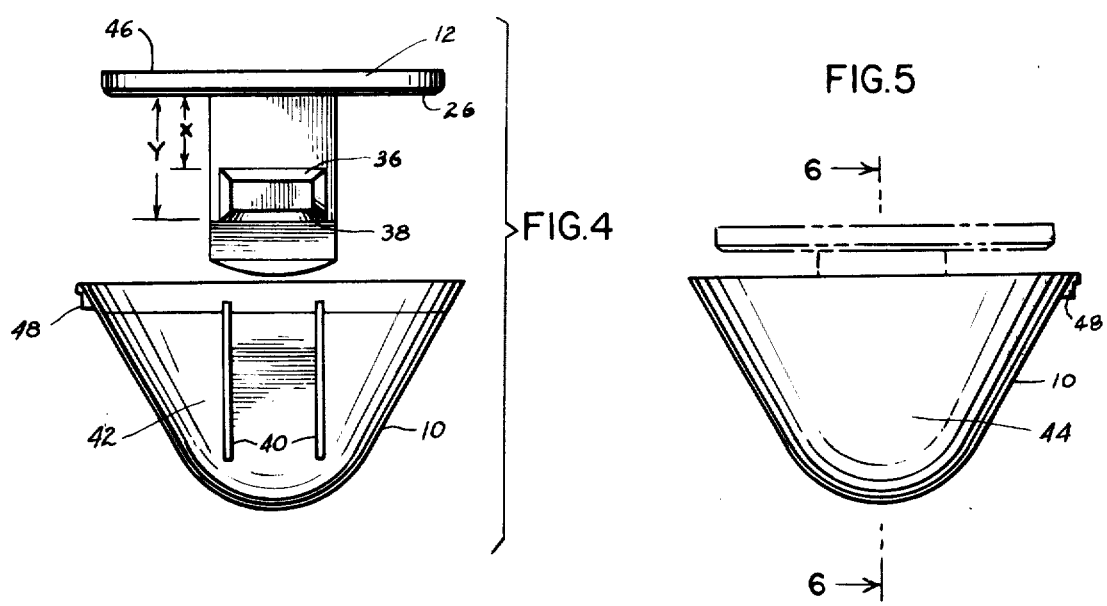
FIG. 4
FIG. 5

DISPENSER FOR AIR TREATING MATERIAL

Air treating gels of the type disclosed in U.S. Pat. No. 2,691,615 as well as other air treating materials provide effective means for gradual introduction into air of volatile air treating components such as air freshening and odor counteractant components. In the packaging of these volatile materials for commercial use, it is desirable to utilize dispensers which provide adequate retention of the material, which are attractive and simple in construction and which, most importantly, provide an effective mechanism for controlling and varying the rate of evaporation of the air treating material during use while preventing loss of material during periods of non-use. It is also desirable that the air treating material can be readily introduced into the dispenser and that the generally unattractive residue of the spent gel be substantially hidden from view. Typical prior art dispensers are disclosed in U.S. Pat. Nos. 2,765,950; 2,765,951; 2,878,060; and 3,239,145.

Thus, the primary object of this invention is to provide a dispenser in which the closure means can be readily supported in varying vertically adjustable positions relative to the base container so as to provide complete closure or varying degrees of openness in controlling the emission of volatilizable material therefrom.

A further object is to provide a dispenser which provides substantially all of the other above-noted prerequisites of an acceptable dispenser.

Another object is to form the dispensers in tandem of two or more interconnected units in order to provide greater flexibility of use.

In general, the dispenser of this invention is constituted by a base container for housing the air treating material which is provided with a generally centrally located socket member and a cover for said container having resilient prongs projecting therefrom for insertion in the socket. The outer surface of each prong exhibits at least one and preferably a plurality of spaced detent means which engage the socket so as to respectively lock the cover in a closed position or in an elevated position at pre-determined distances from said container to permit varying rates of release of the air treating material.

In this manner, maximum control of the rate of the evaporation of the air treating material is achieved. Likewise, greater efficiency and flexibility of emission is achieved in contrast to many conventional air freshener dispensers wherein the emission is inhibited by the nature of the dispenser and thus is dependent solely on convection air currents blowing across the surface of the air treating material. Thus, not only does the instant dispenser allow for this conventional technique as well as for emission through the socket opening, it also uniquely provides paths for the unimpeded release of the light and heavy volatiles in the air treating material around the entire circumferential open area between container and cover. Accordingly, only a small opening of the cover is required to provide sufficient odor counteraction for most conventional needs. With the large and readily accessible reservoir for the air treating material, charging the material into the dispenser is greatly simplified. The relationship between cover and container and the need for providing only a small opening of the cover during operation allows for maximum hiding of any unattractive gel residue. As an optional feature, two or more of the individual dispenser units may be formed in tandem so as to retain the basic properties of the individual units while providing a convenient and attractive assembly for counteracting odors in large enclosed areas.

To the accomplishment of the above, and to such other objects as may hereinafter appear, the present invention relates to the construction of a dispenser for air treating material as defined in the appended claims and as described in this specification taken together with the accompanying drawings, in which:

FIG. 1 is a top plan view of a two unit dispenser of this invention with the first unit having the cover in place and the second unit having the cover removed to expose the interior or the second container and the bottom view of the removed cover;

FIG. 2 is an exploded side elevational view of the instant dispenser;

FIG. 3 is a bottom plan view of the inverted two unit dispenser of FIG. 1;

FIG. 4 is an exploded end elevational view of the dispenser;

FIG. 5 is an opposing end view of the dispenser with the cover in closed position and also showing the cover, in phantom, in the operative position;

Figure 6:
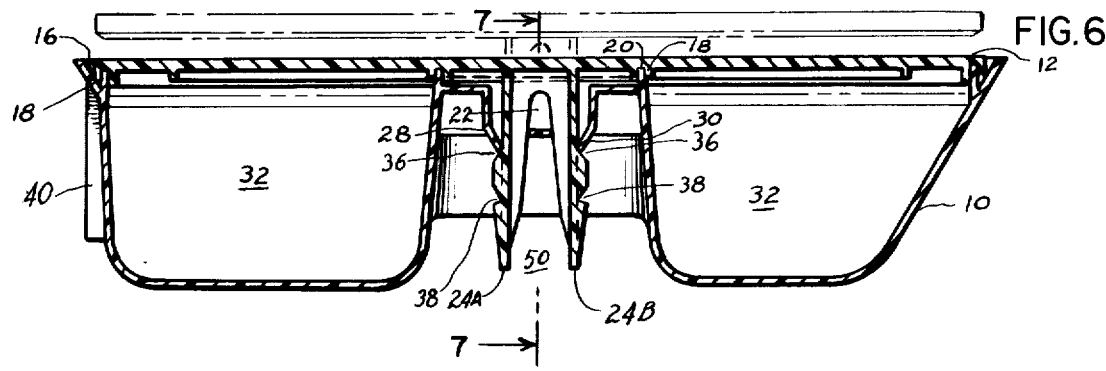
FIG. 6 is a cross-sectional view of the dispenser taken through line 6—6 of FIG. 5.

As shown in FIGS. 1 and 2 of the drawing, the dispensing device comprises a base container 10, generally in tub-like configuration, and a closure or cover 12 having a peripheral recessed channel 14 adapted to receive and closely engage a suitably positioned flange 16 at the upper inside periphery of container 10. The engagement between channel 14 and flange 16 provides a complete seal between container 10 and cover 12. Optionally, cover 12 may contain a centrally located recessed channel 18 adapted to receive a correspondingly positioned flange 20 which is formed by the extension of the outer wall of a socket 22 present in container 10. The latter sealed engagement serves to eliminate evaporation of the air treating material through the socket opening when said dispenser is not in use.

Both container 10 and cover 12 will generally comprise a unitary body of molded plastic material. While these parts are preferably fashioned from polyethylene, polypropylene or polyvinyl chloride, it is to be understood that various types of plastics can be employed, and that the parts can be formed from the same or different plastic materials.

Container 10 is provided with a generally centrally located socket or passage 22 adapted to receive prongs 24 A, B centrally located and extending from the underside 26 of cover 12. The walls of socket 22 terminate in inwardly extending wall sections 28, 30. The remaining interior section 32 of container 10 serves as a reservoir for the air treating material. Optionally, socket 22 may exhibit a transverse cross member 34 for purposes of alignment of prongs 24 A, B and of control of the flexing action thereof. By effecting such control, cross member 34 renders the complete removal of cover 12 more difficult during operation of the dispenser. Such control is advantageous inasmuch as it prevents children, pets, and the like from gaining access to the air treating material.

Although not depicted, the prongs can comprise two straight members with the distance therebetween being less than the distance between the socket walls. In this manner, the engagement resulting from the outward pressure exerted by the resilient prongs against the socket walls serves to position and hold the cover at various vertically spaced distances relative to the container. However, locked engagement is not achieved in this manner.

A more positive and secure positioning technique preferred for purposes of this invention, is provided by resilient prongs 24 A, B as depicted in FIGS. 2 and 4. Thus, prongs 24 A, B are formed to provide a first detent means 36 and a second notched detent means 38 positioned at a pre-determined distance below said first detent means 36. First detent means 36 are positioned at a distance along prongs 24A, B such that when they positively engage wall sections 28, 30, cover 12 will be in a completely sealed position on container 10 (FIG. 6) without any freedom of upward movement. Correspondingly, second detent means 38 are positioned at a distance along prongs 24 A, B such that when they positively engage wall sections 28, 30, cover 12 will be locked in a vertically elevated position relative to container 10 (FIG. 8) to permit evaporation of the air treating material. Accordingly, the relationship (y-x) represents the distance of elevation of cover 12. Needless to say, a plurality of vertically spaced detent means may be provided along the length of the prongs to permit locking of cover 12 in a number of different vertically spaced positions. Prongs 24 A, B are resilient so as to facilitate their compression for purposes of insertion into and removal from socket 22. The bottom section of prongs 24 A, B i.e. the distance between the lower end and detent means 38, is preferably tapered downward (wider at the top) in order to further facilitate the insertion and compression thereof. Likewise, the prong section between said first and second detent means 36, 38 is preferably raised to facilitate release and compression of the prongs 24 A, B during movement from the second detent 38 to the first detent 36.

The dispenser of this invention may include various optional features. For example, FIG. 4 illustrates the presence of integrally molded support members 40 on end 42 which facilitate multi-directional positioning of the dispenser, i.e. the dispenser can preferably be stood on end in a stable upright position in addition to its conventional horizontal positioning. It is to be noted that the opening of cover 12 can be achieved with comparable ease regardless of the manner in which the dispenser is positioned. Likewise, either position exposes to the air the entire circumferential open area between container 10 and cover 12. As noted in FIG. 5, opposite end 44 is devoid of such support members. Alternatively, both ends 42, 44 can be formed with or without such support members, the total absence of support members necessitating the horizontal placement of the dispenser. In addition, the flat upper surface 46 of cover 10 allows for the presence of a virtually unlimited number of graphic designs, decals, labels, and the like thereon. A further optional feature is noted in FIGS. 1 and 3. Thus, the dispenser is produced in tandem comprising two or more individual units joined by linking means 48. Such a tandem dispenser is an attractive and compact vehicle for counteracting odors in large enclosed areas wherein a single dispenser would be insufficient to handle the job and wherein a multiplicity of individual units would be unsightly. It is preferred that linking means 48 be frangible in order to facilitate separation of the individual units where desirable. Linking of the individual units may be accomplished in a number of ways such as those generally noted in U.S. Pat. Nos. 3,520,439 and 3,651,976 wherein the multiple-unit configuration is prepared in a single molding operation.

Figure 7:
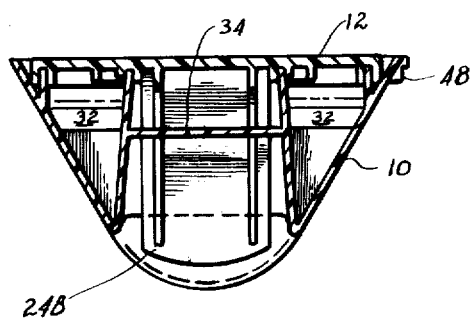
FIG. 7 is a cross-sectional view of the dispenser taken through line 7—7 of FIG. 6.
Figure 8:
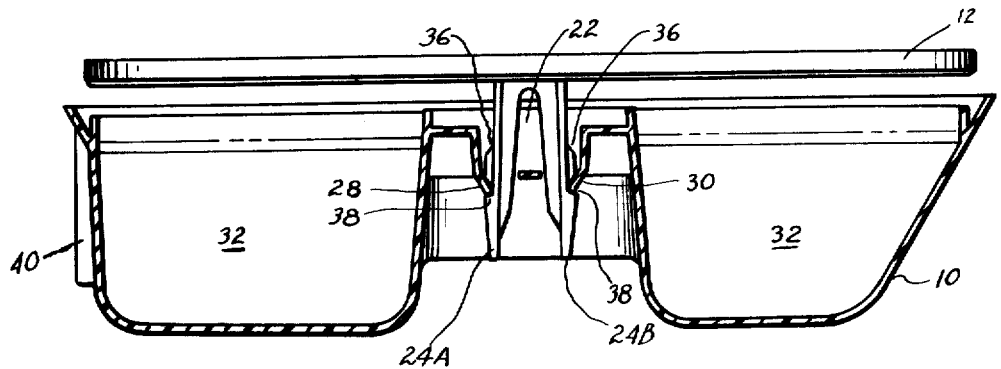
FIG. 8 is a side elevational view, partly in cross-section, showing the dispenser in its operative configuration.

More specifically, the operation of the dispenser of this invention involves the complete separation of container 10 and cover 12 to facilitate charging reservoir 32 with air treating material. For example, air treating gel (U.S. Pat. No. 2,691,615) or other solid air treating material is poured in liquid form into reservoir 32 and permitted to solidify. Likewise, a sponge type solid carrier may be used which merely necessitates pressing the sponge into position. As per FIGS. 6 and 7, prongs 24 A, B of cover 12 are inserted into socket 22 until wall sections 28, 30 are contacted. Inasmuch as the distance between wall sections 28, 30 is less than the distance between prongs 24 A, B, prongs 24 A, B will be compressed and upon further downward pushing, will remain in compressed position until detent means 36 is engaged. Prongs 24 A, B are then released thereby locking cover 12 in a sealed position on container 10. In this manner, there is no evaporation of air treating material. FIG. 8 depicts the dispenser in odor counteracting operation. Thus, prongs 24 A, B which extend into recessed area 50 of container 10, are manually compressed releasing cover 12 from its closed position and elevated until wall sections 28, 30 engage detent means 38. Release of prongs 24 A, B locks cover 12 in the elevated, open position noted in FIG. 8 for emission of air treating material. It should be noted that the practitioner can determine the elevation distance of cover 12 which best suits his particular needs and the nature of his air treating material. In view of the efficient operation of the instant dispenser, a vertical opening of only about 0.125 inch is adequate for satisfactory odor counteraction. When it is desired to reclose the dispenser, cover 12 is pressed down so that prongs 24 A, B are again compressed and lowered until wall sections 28, 30 engage detent means 36. Release of prongs 24 A, B locks the cover in sealed position. Complete removal of cover 12 is accomplished by lifting with manual compression of prongs 24 A, B until detent means 38 clear wall sections 28, 30. However, as noted hereinabove, complete removal of cover 12 is neither desirable from a safety standpoint nor necessary during operation. Thus, the width of cross member 34 is so established that it prevents prongs 24 A, B from closing sufficiently to clear detent 38 from wall sections 28, 30 upon lifting cover 12. Accordingly, additional manual exertion is required to completely remove cover 12.

As noted hereinabove, emission of the air treating material may be uniquely effected in different ways. For example, when the dispenser is in an upright position, emission may occur as the result of convection air currents blowing across the surface of the air treating material. Furthermore, the opening around the entire perimeter of the container allows for the unimpeded upward escape of water and the light volatile components and the comparably unimpeded downward escape of the heavy volatile components. Such movement in effect creates a vacuum between the cover and the gel surface so as to create an in-situ movement of air. As such, the dispenser need not rely solely on the conventional convection approach.

It will be recognized that cover 12 and container 10 can be opened and extended, or lowered and closed, innumerable times before the air treating material is consumed; evaporation progressing only when the dispenser is open and being arrested when the dispenser is closed. When a gel is utilized, the progressive evaporation shrinks the gel mass into an unattractive residue. However, the residue is virtually hidden from view as a result of the expanse of the cover and the need for only a rather narrow opening to expose the air treating material to air currents. Other noticeable advantages of the instant dispenser include maximum control and variability of the release rate of the air treating material, an attractive and simple construction, ease of introduction of the air treating material, and the like.

Summarizing, it is seen that this invention provides an improved dispenser for air treating materials having a unique mechanism for locking the cover in an elevated position in order to effect emission of the air treating material.

While the invention has been described in terms of the specific embodiments herein, it should be apparent that variations may be developed without departing from the spirit or scope of the invention.

What is claimed is:

1. A dispenser for solid volatile materials comprising a container for said volatile material having a socket therein, said socket having two opposing walls terminating in inwardly extending sections; and a cover for said container having at least two resilient prongs extending therefrom insertable and engagingly receivable in the socket of said container, the outer surface of each of said prongs having a first detent means and at least one second detent means positioned at a greater distance from said cover than said first detent means, the positive engagement of said first detent means and said inwardly extending sections effecting the closure of the cover on said container and the positive engagement of said at least one second detent means and said inwardly extending sections resulting in the elevated positioning of said cover with respect to said container.

2. The dispenser of claim 1, wherein a section of each of said prongs below said at least one second detent means is tapered downward.

3. The dispenser of claim 1, wherein the surface of each of said prongs between said first detent means and said at least one second detent means is raised to facilitate release and compression of said prongs.

4. The dispenser of claim 1, wherein at least one end of said container has supporting means for supporting said dispenser in a vertical upright position.

5. The dispenser of claim 1, wherein said socket has an upwardly extending outer wall and said cover has a channel surrounding said prongs, the extended wall and the channel being positioned relative to one another such that they are sealingly engaged when said cover is in a closed position on said container.

6. A multi-unit dispenser for solid volatile materials comprising at least two dispensers according to claim 1 joined along their length by at least one frangible linking means.

7. The dispenser of claim 1, wherein means are positioned in said socket intermediate and parallel to said inwardly extending sections for limiting the inward resilient movement of said prongs such that when said prongs are in closest permissible proximity to one another, said at least one second detent means cannot readily pass, in an upward direction, said inwardly extending sections.

8. A dispenser for solid volatile materials comprising a container for said volatile material having support means on one end thereof to support said dispenser in an upright position and a socket centrally located therein having two opposing walls which terminate in inwardly extending sections; and a cover for said container having two resilient prongs extending therefrom, the outer surface of each of said prongs having a first detent means and a second detent means positioned at a greater distance from said cover than said first detent means, the section of each of said prongs below said second detent means being tapered downwards while the surface of each of said prongs between said first and said second detent means being raised; the positive engagement of said first detent means and said inwardly extending sections effecting the closure of the cover on said container and the positive engagement of said second detent means and said inwardly extending sections resulting in the elevated positioning of said cover with respect to said container.

9. A multi-unit dispenser for solid volatile materials comprising at least two dispensers according to claim 8 joined along their length by at least one frangible linking means.

10. The dispenser of claim 8, wherein means are positioned in said socket intermediate and parallel to said inwardly extending sections for limiting the inward resilient movement of said prongs such that when said prongs are in closest permissible proximity to one another, said at least one second detent means cannot readily pass, in an upward direction, said inwardly extending sections.

11. A multi-unit dispenser for solid volatile materials comprising at least two dispensers according to claim 10 joined along their length by at least one frangible linking means.

* * * * *